United States Patent
Mager et al.

(10) Patent No.: US 7,421,879 B2
(45) Date of Patent: Sep. 9, 2008

(54) DEVICE AND METHOD FOR TRANSFERRING A REFERENCE LIQUID INTO A MEASUREMENT APPLIANCE

(75) Inventors: Gerhard Mager, Bad Homburg (DE); Michael Fischer, Zwickau (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 94 days.

(21) Appl. No.: 10/991,443

(22) Filed: Nov. 17, 2004

(65) Prior Publication Data

US 2005/0132774 A1    Jun. 23, 2005

(30) Foreign Application Priority Data

Nov. 18, 2003 (DE) ................. 103 53 937

(51) Int. Cl.
*G01N 21/00* (2006.01)
(52) U.S. Cl. ....................................... 73/1.02
(58) Field of Classification Search .................. 73/1.02, 73/863, 864.81, 864.73, 864.74, 864.23; 422/81, 104, 102; 222/173, 175, 183; 141/311 R, 141/373
See application file for complete search history.

(56) References Cited

U.S. PATENT DOCUMENTS

| | | | |
|---|---|---|---|
| 3,603,156 A * | 9/1971 | Konkol | 73/864.02 |
| 4,275,774 A | 6/1981 | Andersen et al. | |
| 4,361,253 A | 11/1982 | Flynn et al. | |
| 4,935,373 A * | 6/1990 | Christiansen | 436/18 |
| 5,134,251 A * | 7/1992 | Martin | 174/136 |
| 5,185,263 A * | 2/1993 | Kroneis et al. | 436/8 |
| 5,956,130 A * | 9/1999 | Vancaillie et al. | 356/39 |
| 6,016,683 A * | 1/2000 | Betts et al. | 73/1.03 |
| 6,841,132 B2 * | 1/2005 | Samsoondar | 422/102 |
| 2003/0077303 A1 * | 4/2003 | Holmberg et al. | 424/400 |
| 2005/0209555 A1 * | 9/2005 | Middleton et al. | 604/82 |

OTHER PUBLICATIONS

Definition "conduit" from THEFREEDICTIONARY, 2007.*
Definition "conduit" from American Heritage Dictionary. 1982.*
Definition "ampoule" from THEFREEDICTIONARY, 2007.*

* cited by examiner

*Primary Examiner*—Robert R Raevis
(74) *Attorney, Agent, or Firm*—Kenyon & Kenyon LLP

(57) ABSTRACT

A device for introducing a reference liquid into a measurement appliance for determining the parameters of liquid samples. The device has a separate conduit element which at one end can be inserted into an input port on the measurement appliance and at the other end can be inserted into an ampoule containing the reference liquid. The device also comprises a holding arrangement for holding the ampoule containing the reference liquid, which holding arrangement can be secured on the measurement appliance. There is provided the advantage of affording a high degree of reproducibility between successive introductions. There is also provided a measurement appliance with such a device, and a method for introducing a reference liquid into a measurement appliance.

16 Claims, 3 Drawing Sheets

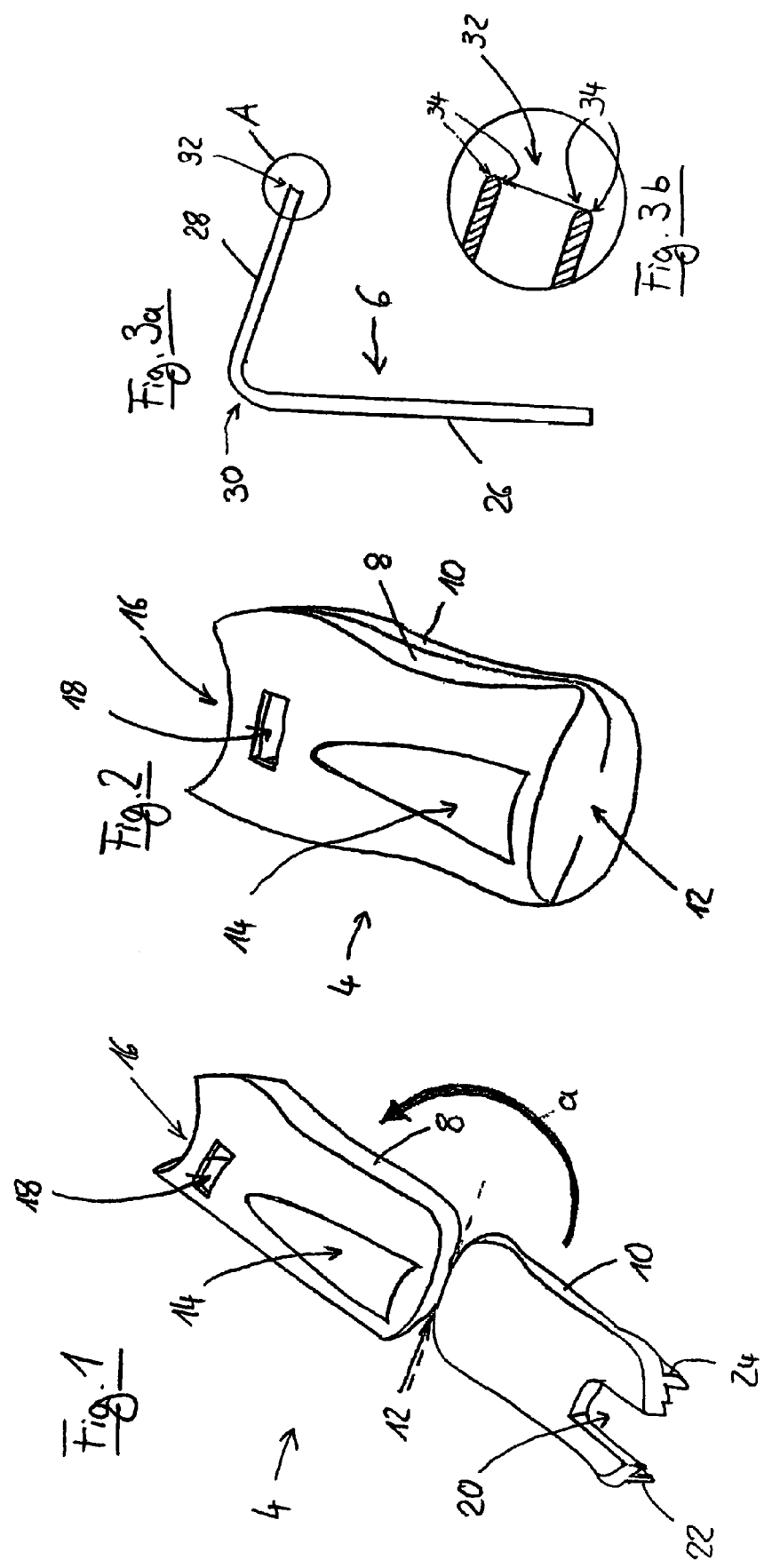

DEVICE AND METHOD FOR TRANSFERRING A REFERENCE LIQUID INTO A MEASUREMENT APPLIANCE

FIELD OF THE INVENTION

The present invention relates to a device and a method for introducing a reference liquid into a measurement appliance for determining the parameters of liquid samples. The invention further relates to a measurement appliance with said device.

BACKGROUND

Various measurement appliances for determining the parameters of liquid samples are known. For example, there exist measurement appliances for determining the parameters and properties of blood samples. For example, blood gases (p02, pC02, p13), electrolytes (Na, K, Ca, Cl) and the conductivity of a sample can be determined with the aid of such measurement appliances.

In medical technology in particular, it is necessary for the measurement appliances to deliver very precise measured values of, for example, the physiological blood parameters of a patient. For this reason, the measurement appliances must be regularly checked for measurement accuracy. For quality control purposes, the entire measurement system, including its calibration media and calibration functions, is desirably inspected for correct functioning.

To check the measurement accuracy, a sample with a known content of all the analytes is measured. If the deviations between measured value and predefined value are below a certain level, this suggests correct functioning of the measurement system. If the deviations are greater than is desirable, the measurement system should not be used to measure a sample from a patient until appropriate repair or maintenance procedures have been undertaken to return it to a state in which the quality control criteria are satisfied. The quality control measurement and its results should be documented.

The reference liquid for checking the measurement accuracy is generally provided in closed ampoules which are not opened until just before use, so as to avoid contaminating or otherwise affecting the reference liquid. To ensure that the measurement results using the reference liquid are not distorted, great care must be taken when introducing the reference liquid into the measurement appliance. In the prior art, this is mainly done by the methods described below.

To remove the reference liquid from the ampoule, a syringe with an attached hollow needle is often used. The hollow needle is inserted into the ampoule in order then to draw the reference liquid by suction into the syringe barrel. When the syringe barrel has been sufficiently filled, the hollow needle can be removed from the syringe. Thereafter, the operator holds the syringe with the open end upwards and taps lightly on the syringe barrel several times so that the air, which as a result of the suction has necessarily been drawn into the reference liquid, collects in the front portion of the syringe barrel. Finally, the syringe plunger is pushed forward until the air collected in the front portion has been completely expelled. A syringe prepared in this manner can now be inserted into an input port of the measurement appliance in order to then inject the reference liquid into this. In the known method, it is also possible to do without a hollow needle.

The method described above has various disadvantages. For instance, the method takes up a great deal of the operator's time. Moreover, if the reference liquid is sucked out too sharply, there is a risk of air in the form of microbubbles getting into the reference liquid, especially if the syringe with the syringe barrel and the syringe plunger does not guarantee sufficient leaktightness. In addition, the reference liquid comes into contact with many new surfaces inside the syringe, increasing the risk of contamination of the reference liquid. Furthermore, there is no reproducibility of the conditions of introduction of the reference liquid.

To overcome these disadvantages, U.S. Pat. No. 4,275,774 describes a device for introducing a reference liquid into a measurement appliance, which device is very much like a syringe. The known device has a hollow space into which an opened ampoule is inserted and in which said inserted ampoule is locked. The known device also has a small tube arranged fixedly in the hollow chamber. The small tube reaches at one end into the inserted ampoule and at the other end leads to an outlet piece which is finally inserted into the input port of the measurement appliance. The hollow space is in communication with a pressure chamber, and the pressure in the pressure chamber can be increased or lowered with a displaceable plunger. To transfer the reference liquid into the measurement appliance, the outlet piece is inserted into the input port, and the pressure in the pressure chamber is then increased with the aid of the plunger. This pressure now acts on the surface of the reference liquid within the ampoule and drives the reference liquid through the small tube and into the measurement appliance.

The known device has the advantage that there is only a small air inclusion in the reference liquid which is introduced. Moreover, the reference liquid comes into contact with fewer new surfaces, so that there is less risk of contamination of the liquid. Nevertheless, using this device still requires a significant amount of time, and exact reproducibility of the introduction of the reference liquid into the measurement appliance is not guaranteed.

Besides the above-described methods and devices in which the pressure for introducing the reference liquid has to be applied by the operator, methods are also known in which the reference liquid is sucked in by the measurement appliance itself. Thus, for example, methods are employed in which a conduit is inserted at one end into the input port and at the other end into the ampoule, so that the measurement appliance can suck the reference liquid in through the conduit.

This method has the advantage that the reference liquid has few air inclusions and comes into contact with few new surfaces, thus largely avoiding contamination.

The pressure or underpressure applied during the introduction is also substantially constant, so that reproducibility of the transfer operations is improved. Despite these improvements, the reproducibility is still not always optimal.

To remove reference liquid from the ampoule, there is also often used a hollow needle which is implemented in the appliance. The hollow needle is inserted into the opened ampoule in order then to suck the reference liquid into the appliance. When sufficient reference liquid has been withdrawn from the ampoule, said ampoule can be detached from the hollow needle.

During the withdrawal of the reference liquid by the appliance, the operator has to hold and position the ampoule by hand via the hollow needle. The operator must ensure that the hollow needle is located within the liquid volume during suction, so as to avoid suctioning of atmospheric air. For subsequent analyses, the hollow needle implemented in the appliance must be cleaned both on the inside and on the outside in order to remove any liquid residues. The above method has various disadvantages. Thus, this method takes up a great deal of the operator's time. During the withdrawal of the liquid, the operator positions the ampoule and the hollow needle. The introduction operation, being specific to the individual user, reduces the reproducibility of the conditions of introduction of the reference liquid.

Moreover, positioning by hand entails the risk of introducing air bubbles instead of the reference liquid into the appliance. The hollow needle means that cleaning is necessary both on the inside and outside after withdrawal of the reference liquid. In the subsequent analyses, liquid residues lead to false results. As the cleaning operation is individual to the user, the reproducibility of the subsequent analyses is reduced.

Another conventional method involves withdrawing the reference liquid without the assistance of the operator. A storage receptacle holding a large number of ampoules or pouches filled with reference liquid is located in or on the appliance. To withdraw the reference liquid from the ampoule or the pouch, these are opened destructively. The introduction of the reference liquid into the appliance is preferably done by suctioning the reference liquid and conveying it through a liquid transport system. The withdrawal of the reference liquid is controlled automatically by the appliance.

This method also has various disadvantages. On account of the storage receptacle used, individual preparation for the measurement of the reference liquid is not guaranteed. Individual preparations are required, for example, as a result of different storage conditions. Parameters of influence are temperature and the state of equilibrium of the reference liquid and surrounding gas atmosphere.

The fluid system installed permanently in the appliance requires cleaning of the liquid-conveying channels after each withdrawal of reference liquid. Liquid residues lead to false measured results in the subsequent analyses.

A further disadvantage also arises from the fluid system installed permanently in the appliance. The fixed positioning of the ampoules or pouches results in very long paths of transport of the fluid system. The partial pressure measured values may be distorted by atmospheric air. In addition, the reference liquid comes into contact with many new surfaces inside the fluid system, thus increasing the risk of contamination of the reference liquid. Thus, there is a need for a device for introducing a reference liquid into a measurement appliance, and also a suitable measurement appliance, where introduction of the reference liquid into the measurement appliance can at all times be carried out under approximately identical conditions. There is also a need for a method for introducing a reference liquid into a measurement appliance for determining the parameters of liquid samples, such that the introduction of the reference liquid can at all times be carried out under approximately identical conditions.

SUMMARY OF THE INVENTION

The device, according to one embodiment of the present invention, is used for introducing a reference liquid into a measurement appliance, with the aid of which the parameters of liquid samples can be determined. The device comprises a separate conduit element. The conduit element can, for example, be a small tube of rigid design and made of glass, plastic or metal. The conduit element can be inserted at one end into an input port on the measurement appliance and at the other end into an ampoule containing the reference liquid. According to one embodiment of the present invention, the device further comprises a holding arrangement for holding the ampoule containing the reference liquid, which holding arrangement can be secured on the measurement appliance.

The securing can be obtained by providing corresponding securing means on the holding arrangement and on the measurement appliance.

In another embodiment of the present invention, there is provided the holding arrangement with a fastening means which can be arranged almost anywhere on the measurement appliance, for example a suction cup or the like. The measurement appliance is in this case designed such that it can suction the reference liquid from the ampoule.

In order to introduce the reference liquid, the conduit element is first inserted into the input port, and the free end is then inserted into the open ampoule. The ampoule can then be introduced into the holding arrangement which has already been secured on the measurement appliance. Thereafter, the measurement appliance can suction the reference liquid through the conduit element from the ampoule.

In addition to the advantages already afforded by the conventional devices, the device according to the invention has the further advantage of ensuring optimal reproducibility of introduction. When successive measurements are carried out on reference liquids from different ampoules, approximately the same conditions prevail, since each further ampoule simply has to be secured again on the holding arrangement in the same orientation to the input port as the preceding ampoule. In addition, handling is easier and less time-consuming since the operator no longer has to hold the ampoule but instead can secure it in the holding arrangement.

In a particularly preferred embodiment of the device according to the invention, the holding arrangement has a depression into which the ampoule can be introduced. The ampoule can be placed in such a depression without the need for any additional fastening means. This ensures rapid introduction and removal of full and empty ampoules, respectively, so that still more time can be saved.

To achieve particularly good reproducibility of the introduction of the reference liquid, the shape of the depression is such that inserted ampoules of same shape and size always have the same spatial orientation. For this purpose, the shape of the depression is preferably such that it corresponds to the shape at least of part of the ampoule. The shape of the depression further preferably corresponds to part of a cylinder, especially as most ampoules have a cylindrical bottom portion. The device of the present invention, according to various embodiments, provides for an exact reproducibility of the position of the ampoule in the depression, as a result of which the reproducibility of the introduction of the reference liquid is provided.

In a further preferred embodiment of the invention, the holding arrangement is configured in such a way that the held ampoule is slanted.

To ensure particularly simple handling, the holding arrangement in a preferred embodiment of the invention has a first part and a second part which are connected to one another in a hinged manner and can be folded together. In such a design, the holding arrangement can be made, for example, from a single injection-molded piece in which the two parts are interconnected via a flexible portion. By folding it together, the holding arrangement can be secured on a projecting shoulder of the measurement appliance. The two parts thus enclose the projecting shoulder.

To avoid damaging the input port, the conduit element in a further preferred embodiment of the invention has rounded edges at its end for insertion into the input port.

The measurement appliance according to the invention for determining the parameters of liquid samples has a holding arrangement for holding an ampoule in which a reference liquid is contained. The holding arrangement is positioned in the area of an input port on the measurement appliance so that a separate conduit element, for example a small tube, can be inserted at one end into the input port and at the other end into the opened ampoule.

To make handling easier for the operator, the holding arrangement of the measurement appliance, according to one embodiment of the present invention, is made in one piece with the measurement appliance so that prior securing of the holding arrangement on the measurement appliance is not needed.

In a particularly preferred embodiment of the invention, and as shown in FIG. 5, the holding arrangement is made in one piece with a closure part for the input port. Since the holding arrangement is integrated in the closure part, the number of parts is reduced and handling thus made easier. Moreover, the closure part and thus the holding arrangement are arranged in direct proximity to the input port, so that the transfer path for the reference liquid can be made short. The risk of contamination is thus further reduced.

The holding arrangement can be a component part of the appliance. It can be easily removed from the latter and cleaned. It can be designed as a "limited use" article intended for a limited period of application. It can also be a component part of a disposable article, in particular a measurement cartridge.

The measurement appliance preferably has a measurement cartridge which contains the flow channels and the sensors for the liquid samples and which can be removed from the measurement appliance. The input port and the holding arrangement are preferably provided on the measurement cartridge. After several measurements, the measurement cartridge can be easily disposed of and replaced by a new one. Such a measurement appliance with disposable cartridge is thus eminently suitable for use in smaller medical practices and the like, where regular and time-consuming maintenance of the measurement appliance would be impractical. However, the device for introducing the reference liquid can also be provided on the actual measurement appliance.

According to one embodiment of the present invention, there is provided a method for introducing a reference liquid into a measurement appliance for determining the parameters of liquid samples that includes the following steps. First, a conduit element is inserted into the input port of the measurement appliance. Then the conduit element is inserted into the opened ampoule containing the reference liquid. Thereafter, the ampoule is introduced into a holding arrangement arranged on the measurement appliance. The holding arrangement is preferably designed as one of the holding arrangements described above. These method steps can be carried out in any desired sequence. Finally, the reference liquid is suctioned through the measurement appliance. As regards the advantages of the method according to the invention, reference is made to the above description of the device and of the measurement appliance.

BRIEF DESCRIPTION OF THE DRAWINGS

The invention is explained further below for one illustrative embodiment, with reference to the attached figures, in which:

FIG. 1 shows a perspective view of the holding arrangement of the device in the folded-out state, according to one embodiment of the present invention;

FIG. 2 shows a perspective view of the holding arrangement from FIG. 1 in the state when folded together;

FIG. 3a shows a side view of the conduit element of the device according to one embodiment of the present invention;

FIG. 3b shows the detail A from FIG. 3a in cross section; and

DETAILED DESCRIPTION

Figure 4:
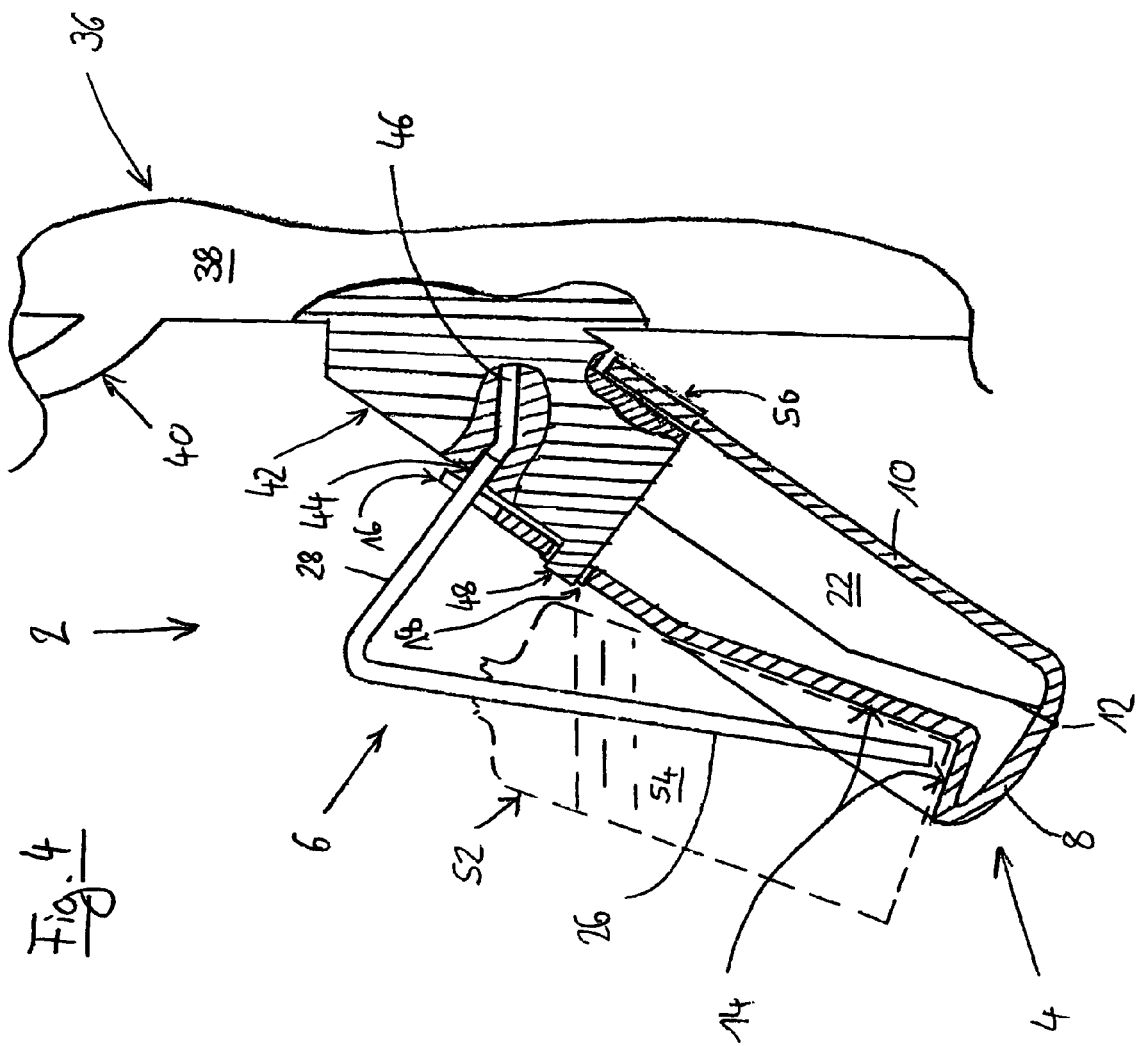
FIG. 4 shows a side view, in cross section, of the device according to the invention arranged as a measurement appliance, together with the holding arrangement and the conduit element from FIGS. 1 to 3b.
Figure 5:
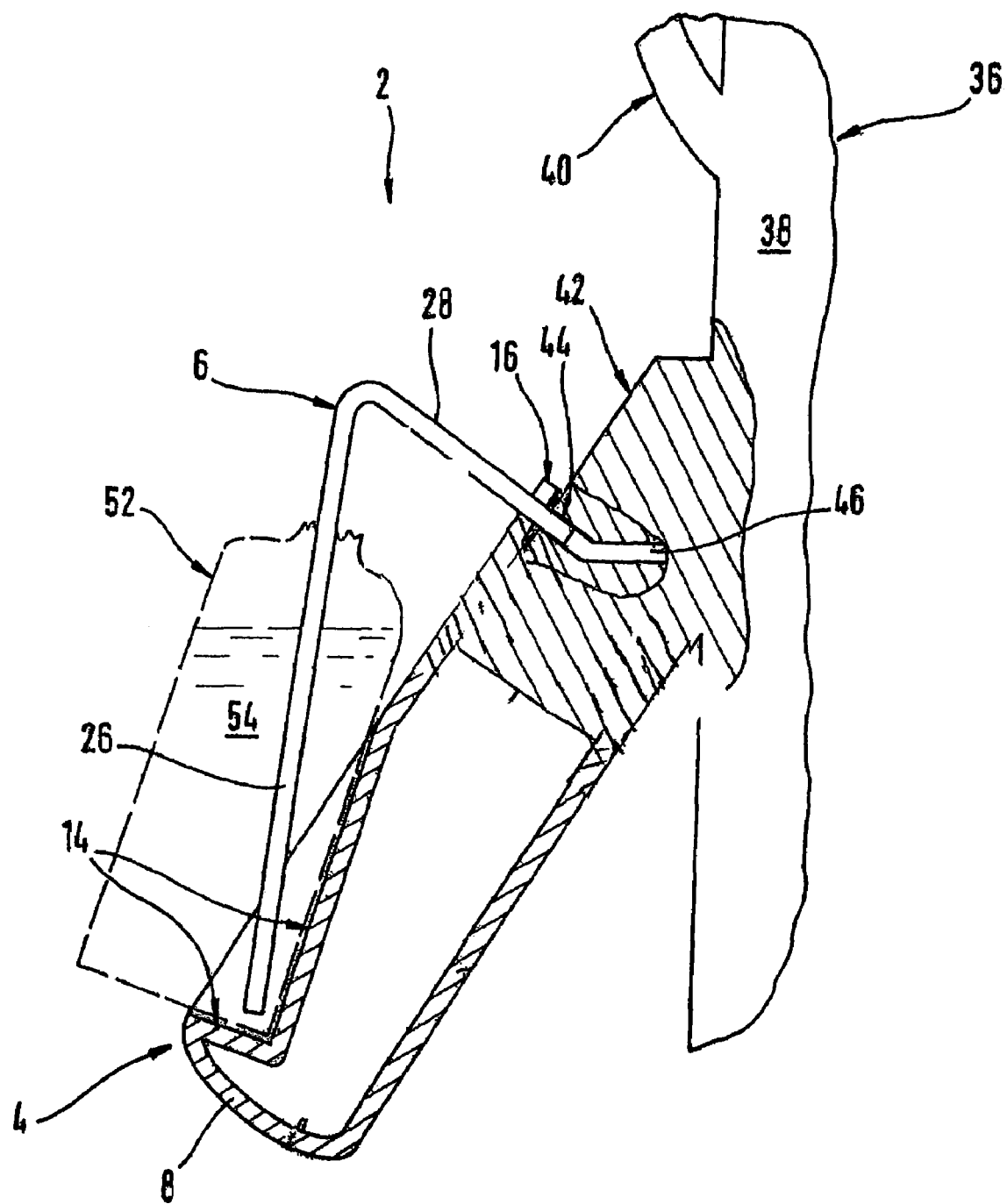
FIG. 5 shows a side view, in cross section, of the device according to the invention, wherein the holding device is made in one piece with the measurement appliance.

A device 2 for introducing a reference liquid into a measurement appliance, according to one embodiment of the present invention, includes a holding arrangement 4 (see for instance FIGS. 1 and 2) and a conduit element 6 (see for instance FIGS. 3a and 3b).

FIG. 1 shows the holding arrangement 4 in the state when folded out. The holding arrangement 4 has a first part 8 and a second part 10 which are connected to one another in an articulated manner via a hinge 12. In the embodiment shown, the holding arrangement 4 is designed as a one-piece plastic component, the hinge 12 being formed by a thin and flexible portion between the two parts 8, 10 so as to allow the two parts 8, 10 to be folded together, as is indicated by the arrow a in FIG. 1.

Provided in the first part 8 there is a depression 14 which is accessible from the outside when the holding arrangement 4 is folded together. An ampoule (not shown) containing the reference liquid can be introduced into this depression 14. The depression 14 is configured in such a way that inserted ampoules of same shape may have the same spatial orientation. In the present embodiment, this is achieved by the fact that the shape of the depression 14 matches the shape at least of part of the ampoule. Since customary ampoules always have a cylindrical lower portion, the shape of the depression 14 may correspond to a part of a cylinder. The depression can also be provided with means for clamping the ampoule in place.

At the end of the first part 8 remote from the hinge 12 there is an indent 16 which provides the necessary space for inserting the conduit element 6 into the measurement appliance, as will be explained in more detail later with reference to FIG. 4. Also arranged in the first part 8, between the depression 14 and the indent 16, there is an opening 18 through which a projecting shoulder on the measurement appliance can be guided, by which means the holding arrangement is securely fixed, as will also be described in more detail with reference to FIG. 4.

The second part 10 of the holding arrangement 4 likewise has an indent 20 at its end remote from the hinge 12. The second part 10 is also provided with two parallel and inwardly offset side walls 22, 24 which, in the folded-together state (FIG. 2), e.g., after pivoting about the hinge 12 in the direction of arrow a, lie inside the first part 8, which has a shell configuration.

The conduit element 6 shown in FIG. 3a is designed as a small rigid glass, plastic or metal tube having a first branch 26 and a second branch 28 connected to one another via a curved portion 30. The first branch 26, which will later serve for insertion deep into the opened ampoule, is slightly longer than the second branch 28 which serves to bridge the path between the outlet of the ampoule and an input port in the measurement appliance. The second branch 28 lies on the continuation of the axis of the sample port and extends as far as the intersection of the axis of the sample port and the axis of the ampoule fixed in the holding arrangement, while the first branch 26 of the conduit element 6 extends from the aforementioned intersection to just over the inner base of the ampoule.

The end 32 of the second branch 28 remote from the curved portion 30 is thus intended to be inserted into an input port. Since this has to be done without causing damage, so that the input port also securely closes after removal of the conduit element 6, the edges 34 at the end 32 of the branch 28 are rounded, as can be seen in FIG. 3*b*. The rounding of the edges 34 also permits easier insertion of the end 32. The conduit element 6 is designed as a separate component part which, after just one use, can be discarded and replaced by a new conduit element. This may eliminate the requirement of cleaning or flushing previously used conduit elements.

FIG. 4 shows a part of the measurement appliance 36 together with the holding arrangement 4. The measurement appliance 36 has a measurement cartridge 38 in which the flow channels (not shown) and also the sensors (not shown) for the liquid samples are located. The measurement cartridge 38 is pushed into the measurement appliance 36 and can then be removed from the measurement appliance 36 via the handle 40 and be disposed of. In this embodiment, the holding arrangement is provided on the measurement cartridge. In principle, however, the holding arrangement can also be part of the actual measurement appliance.

Arranged on the measurement cartridge 38 there is a projecting connection shoulder 42 which is accessible from the outside and on which, in the present embodiment, an input port 44 is provided for introduction of a reference liquid. Adjoining the input port 44 there is a delivery line 46 which leads to the flow channels and to the sensors inside the measurement cartridge 38. The downwardly inclined connection shoulder 42 has, on its top face and lower face, respectively, a further projection shoulder 48, 50 (the latter is shown by a broken line).

The procedure involved in introducing the reference liquid into the measurement appliance 36 is described below. First, the two parts 8, 10 of the holding arrangement 4 (FIG. 1) are folded together in the direction of arrow a about the hinge 12, by which means the projecting connection shoulder 42 on the measurement appliance 36 is to be enclosed by the ends of the parts 8, 10 remote from the hinge 12. With correct orientation of the holding arrangement 4, the shoulder 48 on the top face of the connection shoulder 42 extends into or through the opening 18 in the part 8, and the shoulder 50 on the underside of the connection shoulder 42 extends into or through the indent 20 in the part 10, when the two parts 8, 10 are folded together. Moreover, the connection shoulder 42 is laterally enclosed by the inwardly offset side walls 22, 24 in the part 10.

The opening 18 and the shoulder 48 are adapted to one another so that there is only a slight play when the shoulder 48 protrudes into the opening 18, so as to ensure a reliable and stable arrangement between holding arrangement 4 and the connection shoulder 42. The same applies to the shoulder 50 and the indent 20. The two side walls 22, 24, also bear relatively tightly on the connection shoulder 42.

Elements can also be provided on the two parts 8, 10 of the holding arrangement to ensure that the two parts 8, 10 remain in this folded-together position. For example, locking hooks may be employed for this purpose. Moreover, elements could also be provided on the shoulder 48 which engage behind the edge of the opening 18 after the parts 8, 10 have been folded together, so that a more secure fastening is obtained. The same applies to the shoulder 50 shown by broken lines in FIG. 4.

After the holding arrangement 4 is secured on the measurement appliance 36 or measurement cartridge 38, the conduit element 6 is inserted with the end 32 of the second branch 28 into the input port 44, and the first branch 26 of the conduit element 6 is then inserted into the opened ampoule 52 indicated by broken lines in FIG. 4. The second branch 28 extends through the indent 16 in the part 8 of the holding arrangement 4. The indent 16 thus ensures that the holding arrangement 4 can be arranged as close as possible to the input port 44 without covering the latter. The shorter transfer path thus obtained between the ampoule 52 and the input port 44 permits a shorter conduit element.

The ampoule 52, whose lower portion is of cylindrical configuration, is then introduced into the depression 14 in the holding arrangement 4. At this stage, any holding by the operator of the ampoule 52 may be eliminated. Finally, the measurement appliance can suck the reference liquid 54 through the first branch 26, the curved portion 30 and the second branch 28 via the input port 44 and into the delivery line 46 in order to carry out the measurement of the reference liquid 54 which has been sucked in.

The particular advantage of the device, according to various embodiments of the present invention, lies in the exact reproducibility of successive suction operations, since an ampoule can be disposed in the same orientation as an ampoule from a previous measurement. A high level of reproducibility of the introductions is thus provided, which may provide to great precision in the calibration of the measurement appliance.

What is claimed is:

1. A kit for introducing a reference liquid into a measurement appliance for determining the parameters of liquid samples, comprising:
  a removable conduit element having a proximal end and a distal end, the proximal end being configured to connect to an input port on the measurement appliance and the distal end being configured to connect to a first ampoule containing the reference liquid; and
  a holding device removably securable on the measurement appliance configured to hold the first ampoule,
  wherein the holding device is removably securable on the measurement appliance by means other than the conduit element, and
  wherein the removable conduit element is external to and separate from the holding device and the measurement appliance.

2. The kit according to claim 1, wherein the holding device has a depression configured to receive a first ampoule.

3. The kit according to claim 2, wherein the depression is configured to receive a second ampoule to replace the first ampoule, wherein the first ampoule and the second ampoule have a similar shape.

4. The kit according to claim 3, wherein the shape of the depression is such that the first ampoule and the second ampoule have the same spatial orientation when received by the holding device.

5. The kit according to claim 3, wherein the depression has a shape that corresponds to the shape of at least part of the first ampoule or the second ampoule.

6. The kit according to claim 2, wherein the depression has a shape that corresponds to a part of a cylinder.

7. The kit according to claim 1, wherein the holding device is configured to hold the first ampoule in a slanted position.

8. The kit according to claim 1, wherein the holding device has a first part and a second part connected by a hinge and foldable relative to each other, and wherein the holding device is securable on a projecting shoulder of the measurement appliance.

9. The device of claim 8, wherein the first part and the second part together enclose at least a section of the projecting shoulder of the measurement appliance.

10. The device of claim 8, wherein the first part and the second part further include an opening and at least a section of the projecting shoulder of the measurement appliance extends through the opening.

11. The kit according to claim 1, wherein the proximal end of the conduit element has rounded edges.

12. The device of claim 1, further comprising the ampoule.

13. A measurement appliance for determining the parameters of liquid samples, comprising:
   an input port;
   a holding device for holding an ampoule containing a reference liquid;
   a removable conduit element having a proximal end inserted into the input port and a distal end insertable into the ampoule, and
   a removable measurement cartridge containing flow channels and sensors for the liquid samples and on which the input port is provided and the holding device is mounted.

14. The measurement appliance according to claim 13, wherein the holding device is one integral piece with the measurement cartridge.

15. The measurement appliance according to claim 13, wherein the holding device is one integral piece with the input port.

16. A device for introducing a reference liquid into a measurement appliance having an input port comprising:
   an ampoule containing the reference liquid;
   a removable conduit element having a proximal end and a distal end, the proximal end being configured to connect to the input port on the measurement appliance and the distal end being connected to the ampoule;
   a holding device removably attached to the measurement appliance by means other than the conduit element, said holding device securely holding the ampoule,
   wherein the removable conduit element is external to and separate from the holding device and the measurement appliance.

* * * * *